US009567573B2

(12) United States Patent
Gregory et al.

(10) Patent No.: US 9,567,573 B2
(45) Date of Patent: Feb. 14, 2017

(54) **GENOME EDITING OF A *ROSA* LOCUS USING NUCLEASES**

(75) Inventors: Philip D. Gregory, Orinda, CA (US); Michael C. Holmes, Oakland, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 623 days.

(21) Appl. No.: 13/066,801

(22) Filed: Apr. 25, 2011

(65) Prior Publication Data

US 2011/0265198 A1     Oct. 27, 2011

Related U.S. Application Data

(60) Provisional application No. 61/343,287, filed on Apr. 26, 2010.

(51) Int. Cl.
| C12N 9/22 | (2006.01) |
| A01K 67/027 | (2006.01) |
| C12N 15/10 | (2006.01) |
| C12N 15/90 | (2006.01) |
| A61K 38/00 | (2006.01) |

(52) U.S. Cl.
CPC .............. *C12N 9/22* (2013.01); *A01K 67/0275* (2013.01); *C12N 15/102* (2013.01); *C12N 15/907* (2013.01); *A01K 2207/05* (2013.01); *A01K 2217/07* (2013.01); *A01K 2227/105* (2013.01); *A01K 2267/03* (2013.01); *A61K 38/00* (2013.01); *C07K 2319/81* (2013.01)

(58) Field of Classification Search
CPC ....... C12N 9/1077; C12N 9/96; C12N 15/907; C12N 15/85; C12Y 204/02008
USPC ........ 435/69.1, 366, 455, 372.2, 372.3, 456; 530/350; 536/23.4
See application file for complete search history.

(56) References Cited

U.S. PATENT DOCUMENTS

| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,689,558 B2 | 2/2004 | Case |
| 6,824,978 B1 | 11/2004 | Cox et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,153,949 B2 | 12/2006 | Kim et al. |
| 7,163,824 B2 | 1/2007 | Cox et al. |
| 8,420,782 B2 | 4/2013 | Bonas et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2006/0063231 A1 | 3/2006 | Li et al. |
| 2006/0179502 A1 | 8/2006 | Kauselmann et al. |
| 2006/0188987 A1 | 8/2006 | Guschan et al. |
| 2007/0134796 A1 | 6/2007 | Holmes et al. |
| 2007/0218528 A1 | 9/2007 | Miller et al. |
| 2008/0015164 A1 | 1/2008 | Collingwood |
| 2008/0131962 A1 | 6/2008 | Miller |
| 2008/0159996 A1 | 7/2008 | Ando et al. |
| 2009/0305419 A1 | 12/2009 | Miller et al. |
| 2010/0047805 A1 | 2/2010 | Wang et al. |
| 2011/0201055 A1 | 8/2011 | Doyon et al. |
| 2011/0301073 A1 | 12/2011 | Gregory et al. |
| 2012/0064620 A1* | 3/2012 | Bonas et al. ............... 435/320.1 |
| 2012/0178131 A1* | 7/2012 | Voytas et al. ............... 435/91.52 |

FOREIGN PATENT DOCUMENTS

| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |

(Continued)

OTHER PUBLICATIONS

Kay S et al. A Bacterial Effector Acts as a Plant Transcription Factor and Induces a Cell Size Regulator. 2007. Science. 318:648-651.*
Voytas, et al., "DNA Binding Made Easy," *Science* 326:1491-1492 (2009).
Beerli, et al., "Engineering Polydactyl Zinc-Finger Transcription Factors," *Nature Biotechnology* 20:135-141 (2002).
Bitinate, et al., "FokI Dimerization Is Required for DNA Cleavage," *PNAS USA* 95:10570-10575 (1998).
Boch, et al., "Breaking the Code of DNA Binding Specificity of TAL-Type III Effectors," *Science* 326:1509-1512 (2009).
Choo, et al., "Advances in Zinc Finger Engineering," *Curr. Opin. Struct. Biol.* 10:411-416 (2000).
Isalan et al., "A Rapid, Generally Applicable Method to Engineer Zinc Fingers Illustrated by Targeting the HIV-1 Promoter," *Nat Biotechnol* 19:656-660 (2001).

(Continued)

*Primary Examiner* — Paul Holland
(74) *Attorney, Agent, or Firm* — Pasternak Patent Law; Susan Abrahamson

(57) ABSTRACT

Disclosed herein are methods and compositions for genome editing of a *Rosa* locus, using fusion proteins comprising a DNA binding domain and a cleavage domain or cleavage half-domain. Polynucleotides encoding said fusion proteins are also provided, as are cells comprising said polynucleotides and fusion proteins.

20 Claims, 2 Drawing Sheets

(56) References Cited

FOREIGN PATENT DOCUMENTS

| WO | WO 98/53060 A1 | 11/1998 |
|---|---|---|
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 1/2007 |
| WO | WO 2007/139898 A2 | 12/2007 |
| WO | WO 2008/133938 A2 | 11/2008 |
| WO | WO 2011051390 A1 * | 5/2011 |

OTHER PUBLICATIONS

Kim, et al., "Chimeric Restriction Endonuclease," *PNAS USA* 91:883-887 (1994).

Kim, et al., "Insertion and Deletion Mutants of FOKI Restriction Endonuclease," *J. Biol. Chem.* 269:31978-31982 (1994).

Li, et al., "Functional Domains in FOK I Restriction Endonuclease," *PNAS USA* 89:4275-4279 (1992).

Li, et al., "Alteration of the Cleavage Distance of FOK I Restriction Endonuclease by Insertion Mutagenesis," *PNAS USA* 90:2764-2768 (1993).

Miller, et al., "A Tale Nuclease Architecture for Efficient Genome Editing," *Nature Biotechnology* 29:143-148 (2011).

Moscou, et al., "A Simple Cipher Governs DNA Recognition by TAL Effectors," *Science* 326:1501 (2009).

Nyabi, et al., "Efficient Mouse Transgenesis Using Gateway-Compatible ROSA26 Locus Targeting Vectors and F1 Hybrid ES Cells," *Nucl Acids Res* 37:e55 (2009).

Pabo, et al., "Design and Selection of Novel CYS2-HIS2 Zinc Finger Proteins," *Ann. Rev. Biochem.* 70:313-340 (2001).

Roberts, et al., "Rebase: Restriction Enzymes and Methyltransferases," *Nucleic Acids Research* 31:418-420 (2003).

Segal, et al., "Custom DNA-Binding Proteins Come of Age: Polydactyl Zinc-Finger Proteins," *Curr. Opin. Biotechnol.* 12:632-637 (2001).

Strathdee, et al., "Expression of Transgenes Targeted to the GT(ROSA)26SOR Locus Is Orientation Dependent," *Plos One* 1:e4 (2006).

Porteus et al., Gene Targeting Using Zinc Finger Nucleases, *Nature Biotechnology* 23(8):967-973 (2005).

Soriano et al., Generalized LACZ Expression With ROSA26 CRE Reporter Strain, *Nature Genetics* 21(1):70-71 (1999).

* cited by examiner

SEQUENCE LISTING

```
<160> NUMBER OF SEQ ID NOS: 92

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Gly Glu Lys Pro
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Gly Gly Gln Arg Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 3

Thr Gly Gln Lys Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Gly Ser Gln Lys Pro
1               5

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaaggtacc gggagtggat gaaggagttg                                      30

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaaaccgcgg cggatcacaa gcaataat                                        28

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttcgcggcc gcgatctgca actggagtct ttc                                  33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttcgtttaa acgatctgca actggagtct ttc                                  33

<210> SEQ ID NO 9
<211> LENGTH: 32
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 9
gatcgcggcc gcgaagaagg gggaagggaa tc                                32

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatcgtttaa acgaagaagg gggaagggaa tc                                32

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaaaggtacc gcgtgtgaaa acacaaatgg                                   30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaaaccgcgg aaggaaagag gcattcatgg                                   30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaaaggtacc attatggagg ggaggactgg                                   30

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaaaccgcgg acatgtggca aacaggaga                                    29

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tgtcttctga ggaccgccc                                                19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgcccagaa gactcccgc                                                19

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ser Gly Asp Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly Ser Leu Thr Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Gly His Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ser Ser Asp Leu Thr Arg
1               5

<210> SEQ ID NO 21
<211> LENGTH: 7
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 21

Arg Ser Asp Asn Leu Ser Glu
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Asn Ala His Arg Lys Thr
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Ser Ala Arg Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Gly His Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Asp Asp Leu Ser Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Asn Asp His Arg Lys Asn
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Thr Thr Ser Leu Asp Arg
1               5

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ctagaaagac tggagttgca gatcacga                                      28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gatgggcggg agtcttctgg gcaggctt                                      28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctagaaagac tggagttgca gatcacga                                      28

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggctcgagtg agtcatcaga cttctaagat cagg                               34

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggctcgagtt ttgataaggc tgcagaag                                      28
```

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctgaattcga atgggcggga gtcttctggg ca                                  32

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaagcttgg aggtaggtgg ggtgagg                                        27

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ccaagcttag tcgctctgag ttgttatc                                       28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccaagctttc tgggagttct ctgctgcc                                       28

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cattcgaatt cagaaagact ggagttgcag atc                                 33

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Arg Ser Asp Leu Ser Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp Asp Leu Thr Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Ser Gly His Leu Ser Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Ser Asp Asn Leu Ser Val
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Ala Asn Leu Thr Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ser Asp His Leu Thr Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 44

Asn Ser Ser Asn Leu Ser Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Asp His Leu Thr Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asn Ser Asp His Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp His Leu Ser Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ser Asp His Leu Ser Glu
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ser Ala Ala Leu Ala Arg
1               5

<210> SEQ ID NO 50
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ser Asp His Leu Ser Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Asn Ala His Arg Ile Thr
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Ala Val Leu Ser Glu
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ser Ala Asn Leu Ala Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Asp Asn Leu Arg Glu
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Asn Arg Asp Arg Ile Lys
```

```
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Asp Thr Leu Ser Glu
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Ser Ser His Leu Ala Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Asp Asn Leu Thr Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Ser Ser Thr Arg Lys Thr
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Ser Gly Asn Leu Thr Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 61

Gln Ser Gly Asn Leu Ala Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Ser Asp Ala Leu Ser Val
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Ser Ser His Arg Thr Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Asp Val Leu Ser Glu
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Arg Ser Asn Leu Val Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ser Asp His Leu Thr Gln
1               5

<210> SEQ ID NO 67

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ser Gly His Leu Gln Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Arg Ser His Leu Ala Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Arg Asn His Arg Thr Thr
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Lys Arg Ser Leu Ile Glu
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ser Ser Asn Leu Ser Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72
```

Arg Ser Asp His Leu Ser Ala
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Asn Asp Asn Arg Ile Lys
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asn Asn Arg Asp Leu Ile Asn
1               5

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctgagaaggg tgcggccttt tctccgcc                                      28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
acgggggagg ggagtgttgc aatacctt                                      28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tcctgagaag ggtgcggcct tttctccg                                      28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 ggggaggggga gtgttgcaat acctttct					28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gacaggaggc agcagagaac tcccagaa					28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tctgaggacc gccctgggcc tggaagat					28

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gaagacagga ggcagcagag aactccca					28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaggaccgcc ctgggcctgg aagattcc					28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gtcctcagaa gacaggaggc agcagaga					28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ccctgggcct ggaagattcc cttcccccc                                28

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gcggtcctca gaagacagga ggcagcag                                 28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgggcctgga agattccctt ccccttc                                  28

<210> SEQ ID NO 87
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87 aaggggaag ggaatcttcc aggcccag                                  28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ttccctcgtg atctgcaact ggagtctt                                 28

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gggaagaagg gggaagggaa tcttccag                                 28

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90

-continued

```
gtgatctgca actggagtct ttctggaa                                          28

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cccagctaca gcctcgattt                                                   20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cacaaatggc gtgttttggt                                                   20
```

GENOME EDITING OF A *ROSA* LOCUS USING NUCLEASES

CROSS-REFERENCE TO RELATED APPLICATIONS

The present application claims the benefit of U.S. Provisional Application No. 61/343,287, filed Apr. 26, 2010, the disclosure of which is hereby incorporated by reference in its entirety herein.

STATEMENT OF RIGHTS TO INVENTIONS MADE UNDER FEDERALLY SPONSORED RESEARCH

Not applicable.

TECHNICAL FIELD

The present disclosure is in the fields of genome engineering, including somatic and heritable gene insertions/disruptions, genomic alterations, generation of alleles carrying random mutations and/or insertion of transgenes into a *Rosa* locus.

BACKGROUND

*Rosa* gene products are ubiquitously expressed at all stages of development. As such, this locus has been widely used for expressing endogenous sequences from endogenous or introduced promoters and for creating transgenic mice, for example from embryonic stem cells. See, e.g., Strathdee et al. (2006) *PLoS ONE*, Issue 1, e4; Nyabi et al. (2009) *Nucl. Acids. Res.* 37:e55.

However, conventional methods of targeted insertion can require complicated assembly of target vectors. Thus, there remains a need for methods of targeted insertion into and/or modification of *Rosa* gene in a targeted fashion. Precisely targeted site-specific cleavage of genomic loci offers an efficient supplement and/or alternative to conventional homologous recombination. Creation of a double-strand break (DSB) increases the frequency of homologous recombination at the targeted locus more than 1000-fold. More simply, the imprecise repair of a site-specific DSB by non-homologous end joining (NHEJ) can also result in gene disruption. Creation of two such DSBs results in deletion of arbitrarily large regions. The modular DNA recognition preferences of zinc-fingers protein allows for the rational design of site-specific multi-finger DNA binding proteins. Fusion of the nuclease domain from the Type II restriction enzyme Fok I to site-specific zinc-finger proteins allows for the creation of site-specific nucleases. See, for example, United States Patent Publications 20030232410; 20050208489; 20050026157; 20050064474; 20060188987; 20060063231; 20070134796; 2008015164; 20080131962; 2008015996 and International Publication WOs 07/014,275 and 2008/133938, which all describe use of zinc-finger nucleases and which are incorporated by reference in their entireties for all purposes.

SUMMARY

Disclosed herein are compositions and methods for targeted insertion into a *Rosa* gene locus. The compositions and methods described herein can be used for genome editing, including, but not limited to: cleaving of one or more genes in an animal cell resulting in targeted alteration (insertion, deletion and/or substitution mutations) in one or more genes, including the incorporation of these targeted alterations into the germline; targeted introduction of non-endogenous nucleic acid sequences, the partial or complete inactivation of one or more genes in an animal; methods of inducing homology-directed repair, generation of transgenic animals (e.g., rodents) and/or generation of random mutations encoding novel allelic forms of animal genes.

In one aspect, described herein is a DNA-binding domain that binds to a target site in a *Rosa* gene in a genome (e.g., a rodent genome), for example a DNA binding domain comprising one or more TALE repeat domains or a zinc-finger protein (ZFP). In certain embodiments, the DNA binding domain comprises one or more wild-type (naturally occurring) TALE repeat domains isolated from *Xanthomonas, Ralstonia* or another related bacteria. In other embodiments, the one or more TALE repeat domains is/are non-naturally occurring, for example one or more amino acids in the repeat region (e.g., RVD) is been altered such that the domain binds to a selected target *Rosa* sequence). See, also, U.S. Publication No. 20110301073, incorporated by reference herein in its entirety. Exemplary RVD sequences include NI, HI, AI, CI, DI, EI, RI or KI for recognition of an adenine (A); HD, AD, KD, YD, ED, AD, ND or RD for recognition of a cytosine (C); NN, DK, DH, KN, EN, AN, CN, GN, FN, AK, NK or CK for recognition of guanine (G); and NG, KG, MG, QG, RG, AA, QA, IG, IP, LA, YG, HG, SG, VG, IA or VA for recognition of a thymine (T).

In another aspect, the *Rosa* -binding DNA-binding domain is fused to a nuclease domain that cleaves a target genomic region of interest of the *Rosa* gene, for example a zinc finger nuclease (ZFN) or TALE nuclease (TALEN). In certain embodiments, the nuclease comprises a cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the DNA-binding domain recognizes a target site in a *Rosa* gene, for example *Rosa* 26.

The nuclease (e.g., TALEN) may bind to and/or cleave a *Rosa* gene within the coding region of the gene or in a non-coding sequence within or adjacent to the gene, such as, for example, a leader sequence, trailer sequence or intron, or within a non-transcribed region, either upstream or downstream of the coding region.

In another aspect, described herein are compositions comprising one or more of the nucleases described herein. In certain embodiments, the composition comprises one or more nucleases in combination with a pharmaceutically acceptable excipient.

In another aspect, described herein is a polynucleotide encoding one or more nucleases described herein. The polynucleotide may be, for example, mRNA.

In another aspect, described herein is an expression vector comprising a polynucleotide, encoding one or more nucleases described herein, operably linked to a promoter.

In another aspect, described herein is a host cell comprising one or more *Rosa* -targeted nuclease expression vectors as described herein. The host cell may be stably transformed or transiently transfected or a combination thereof with one or more of the expression vectors described herein. In one embodiment, the host cell is an embryonic stem cell. In other embodiments, the one or more expression vectors express one or more nucleases (e.g., ZFNs or TALENs) in the host cell. In another embodiment, the host cell may further comprise an exogenous polynucleotide donor sequence. In any of the embodiments, described herein, the host cell can comprise an embryo cell, for example a one or more mouse, rat, rabbit or other mammal cell embryo.

In another aspect, described herein is a method for cleaving one or more *Rosa* genes in a cell, the method comprising: (a) introducing, into the cell, one or more polynucleotides encoding one or more nucleases (e.g., TALENs or ZFNs) that bind to a target site in the one or more *Rosa* genes under conditions such that the nuclease(s) is (are) expressed and the one or more genes are cleaved.

In yet another aspect, described herein is a method for introducing an exogenous sequence into the genome of a cell, the method comprising the steps of: (a) introducing, into the cell, one or more polynucleotides encoding one or more nucleases that bind to a target site in a *Rosa* gene under conditions such that the nucleases(s) is (are) expressed and the one or more genes are cleaved; and (b) contacting the cell with an exogenous polynucleotide; such that cleavage of the gene(s) stimulates integration of the exogenous polynucleotide into the genome by homologous recombination. In certain embodiments, the exogenous polynucleotide is integrated physically into the genome. In other embodiments, the exogenous polynucleotide is integrated into the genome by copying of the exogenous sequence into the host cell genome via nucleic acid replication processes (e.g., homology-directed repair of the double strand break). In yet other embodiments, integration into the genome occurs through non-homology dependent targeted integration (e.g. "end-capture"). In certain embodiments, the one or more nucleases are fusions between the cleavage domain of a Type IIS restriction endonuclease and an engineered DNA-binding domain. In certain embodiments, the exogenous sequence is integrated into a small mammal (e.g. rabbit or rodent such as mouse, rat, etc.) *Rosa* gene.

In another embodiment, described herein is a method for modifying one or more *Rosa* gene sequence(s) in the genome of cell, the method comprising (a) providing a cell comprising one or more *Rosa* sequences; and (b) expressing at least one *Rosa*-targeted nuclease in the cell such that the *Rosa* gene is cleaved in at least one site, wherein cleavage of the at least one cleavage site results in modification of the gene sequence by non-homologous end joining and/or homology directed repair. Optionally, the cleavage results in insertion of an exogenous sequence (transgene) also introduced into the cell. In other embodiments, non-homologous end joining results in a deletion between the first and second cleavage sites. The size of the deletion in the gene sequence is determined by the distance between the first and second cleavage sites. Accordingly, deletions of any size, in any genomic region of interest, can be obtained. Deletions of 25, 50, 100, 200, 300, 400, 500, 600, 700, 800, 900, 1,000 nucleotide pairs, or any integral value of nucleotide pairs within this range, can be obtained. In addition deletions of a sequence of any integral value of nucleotide pairs greater than 1,000 nucleotide pairs can be obtained using the methods and compositions disclosed herein. In certain embodiments, first and second nucleases are used to cleave at two sites and the gene sequence located between the first cleavage site and the second cleavage site is modified.

Methods of modifying an endogenous *Rosa* gene as described herein can be used to create models of animal (e.g., human) disease, for example by inactivating (partially or fully) a gene or by creating random mutations at defined positions of genes that allow for the identification or selection of transgenic animals (e.g., rats, rabbits or mice) carrying novel allelic forms of those genes, by insertion of humanized genes (to study, by way of a non-limiting example, drug metabolism) or by insertion of a mutant alleles of interest to examine, for example, the phenotypic affect of such a mutant allele.

In yet another aspect, described herein is a method for germline disruption of one or more target *Rosa* genes, the method comprising modifying one or more *Rosa* sequences in the genome of one or more cells of an embryo by any of the methods described herein and allowing the embryo to develop, wherein that the modified gene sequences are present in at least a portion of gametes of the sexually mature animal. In certain embodiments, the animal is a small mammal, such as a rodent or rabbit.

In another aspect, described herein is a method of creating one or more heritable mutant alleles in at least one *Rosa* locus of interest, the method comprising modifying one or more *Rosa* loci in the genome of one or more cells of an animal embryo by any of the methods described herein; raising the embryo to sexual maturity; and allowing the sexually mature animal to produce offspring; wherein at least some of the offspring comprise the mutant alleles. In certain embodiments, the animal is a small mammal, for example a rabbit or a rodent such as rat, a mouse or a guinea pig.

In any of the methods described herein, the polynucleotide encoding the nuclease(s) can comprise DNA, RNA or combinations thereof. In certain embodiments, the polynucleotide comprises a plasmid. In other embodiments, the polynucleotide encoding the nuclease comprises mRNA.

In a still further aspect, provided herein is a method for site specific integration of a nucleic acid sequence into a *Rosa* locus of a chromosome. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a nuclease (e.g., TALEN) as described herein that recognizes the site of integration in the *Rosa* locus, and (b) culturing the embryo to allow expression of the nuclease, wherein a double stranded break introduced into the site of integration by the nuclease is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of a nuclease (e.g., TALEN). In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a Drosophila embryo or a mosquito embryo.

Also provided is an embryo comprising at least one DNA vector, wherein the DNA vector comprises an upstream sequence and a downstream sequence flanking the nucleic acid sequence to be integrated, and at least one RNA molecule encoding a nuclease that recognizes the chromosomal site of integration. Organisms derived from any of the embryos as described herein are also provided.

A kit, comprising the DNA-binding domains and/or nucleases of the invention, is also provided. The kit may comprise nucleic acids encoding the DNA-binding domains and/or nucleases (e.g. RNA molecules or DNA-binding domain encoding genes contained in a suitable expression vector), donor molecules, suitable host cell lines, instructions for performing the methods of the invention, and the like.

DETAILED DESCRIPTION

Figure 1:
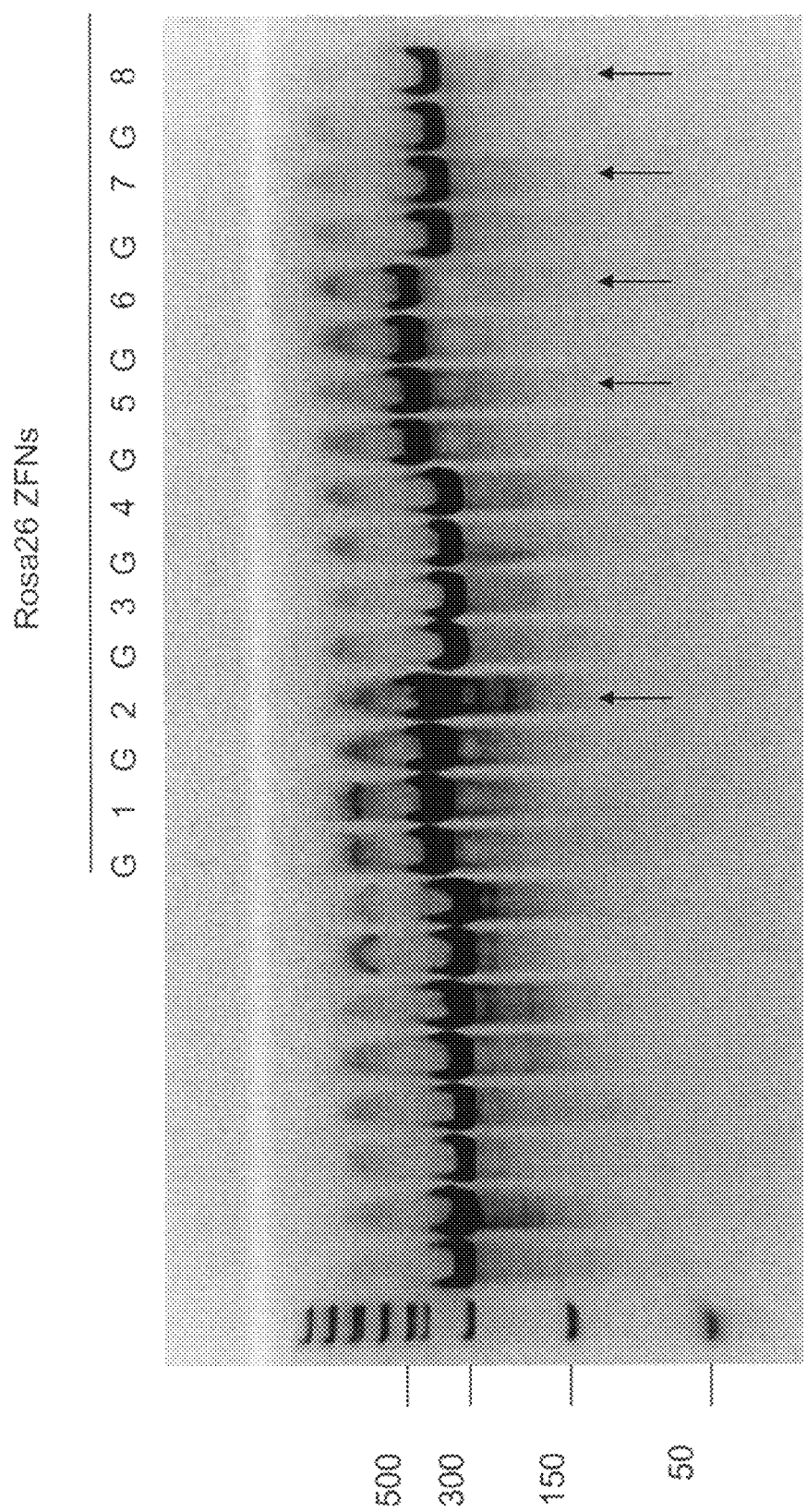
FIG. 1 depicts a Southern blot demonstrating the results of NHEJ repair following cleavage of the rat rosa 26 locus as assayed by the Surveyor™ (Transgenomic) mismatch assay. "G" indicates reactions where cells were transfected with GFP ZFNs, and numbered lanes indicate specific ZFN pairs. Arrows indicate lanes where NHEJ has occurred.

Described herein are compositions and methods for genomic editing in (for example, in small mammals such as mice, rats or rabbits) (e.g., cleaving of genes; alteration of genes, for example by cleavage followed by insertion (physical insertion or insertion by replication via homology-directed repair) of an exogenous sequence and/or cleavage followed by non-homologous end joining (NHEJ); partial on complete inactivation of one or more genes; generation of alleles with random mutations to create altered expression of endogenous genes; etc.) and alterations of the genome which are carried into the germline. Also disclosed are methods of making and using these compositions (reagents), for example to edit (alter) one or more genes in a target animal (e.g., small mammal) cell. Thus, the methods and compositions described herein provide highly efficient methods for targeted gene alteration (e.g., knock-in) and/or knockout (partial or complete) of one or more genes and/or for randomized mutation of the sequence of any target allele, and, therefore, allow for the generation of animal models of human diseases.

The compositions and methods described herein provide rapid, complete, and permanent targeted disruption of endogenous loci in animals without the need for labor-intensive selection and/or screening and with minimal off-target effects. Whole animal gene knockouts can also be readily generated in a single-step by injecting nuclease (e.g., ZFN or TALEN) mRNA or nuclease expression cassettes.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al. CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc-finger proteins have DNA-binding, RNA-binding and protein-binding activity.

A "zinc-finger DNA binding protein" (or binding domain) is a protein, or a domain within a larger protein, that binds DNA in a sequence-specific manner through one or more zinc-fingers, which are regions of amino acid sequence within the binding domain whose structure is stabilized through coordination of a zinc ion. The term zinc-finger DNA binding protein is often abbreviated as zinc-finger protein or ZFP.

A "TALE repeat sequence" is a structural sequence that is involved in the binding of the TALE to its cognate target DNA sequence. These repeats are typically 33-35 amino acids in length and almost invariably exhibit a great deal of sequence homology with other TALE repeat sequences within a TALE protein. Positions 12 and 13 (the RVD) exhibit hypervariability and are thought to be the amino acids that determine what DNA nucleotide the repeat will interact with. The most C-terminal repeat often displays sequence similarity only for the first 20 amino acids and so is referred to as a half repeat. The most N-terminal repeat has a sequence immediately preceding it that shows some similarity to the repeat sequences, and thus is termed the R0 repeat. Typically, the preferred nucleotide to the position immediately 5' of the target site is a thymidine (T). It may be that the R0 repeat prefers to interact with a T adjacent to a target sequence specified by the TALE-repeats.

A "TALE-repeat domain" is a protein, or a domain within a larger protein, that interacts with DNA in a sequence-specific manner through one or more TALE repeat sequences.

DNA binding domains such as TALE domains and zinc finger proteins can be "engineered" to bind to a predetermined nucleotide sequence. Non-limiting examples of methods for engineering such proteins are design and selection. A designed DNA-binding protein is a protein not occurring in nature whose design/composition results principally from rational criteria. Rational criteria for design include application of substitution rules and computerized algorithms for processing information in a database storing information of existing designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" DNA binding protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe.

Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional nucleases can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528 and 2008/0131962, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule. An exogenous molecule can also be a molecule normally found in another species, for example, a human sequence introduced into an animal's genome.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a DNA-binding domain as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as; for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain is fused to a cleavage domain, the DNA-binding domain and the cleavage domain are in operative linkage if, in the fusion polypeptide, the DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Nucleases

Described herein are nucleases (e.g., TALENs or ZFNs) that can be used for genomic editing (e.g., cleavage, alteration, inactivation and/or random mutation) of one or more *Rosa* genes. TALENs comprise one or more TALE repeat domains and a nuclease (cleavage) domain (e.g., cleavage half-domain). ZFNs comprise a zinc-finger protein (ZFP) and a nuclease (cleavage) domain (e.g., cleavage half-domain).

A. DNA-Binding Domains

Any suitable DNA-binding domain can be employed, including zinc finger DNA-binding domains or DNA-binding domains comprising TALE domain sequences. Zinc-finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416.

In other aspects, the DNA binding domain comprises one or more wild-type or one or more engineered domains from a TAL effector (TALE) derived from the plant pathogen Xanthomonas or Ralstonia (see, Miller et al. (2010) *Nature Biotechnology*, Dec 22 [Epub ahead of print]; Boch et al, (2009) *Science* 29 Oct. 2009 (10.1126/science.117881) and Moscou and Bogdanove, (2009) *Science* 29 Oct. 2009 (10.1126/science.1178817); see, also, U.S. Publication No. 20110301073, the disclosures of which is hereby incorporated by reference in its entirety.

An engineered DNA binding domain can have a novel binding specificity, compared to a naturally-occurring zinc-finger protein. Engineering methods include, but are not limited to, rational design and various types of selection. Rational design includes, for example, using databases comprising triplet (or quadruplet) nucleotide sequences and individual zinc-finger amino acid sequences, in which each triplet or quadruplet nucleotide sequence is associated with one or more amino acid sequences of zinc-fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248;

6,140,466; 6,200,759; and 6,242,568; as well as WO 98/37186; WO 98/53057; WO 00/27878; WO 01/88197 and GB 2,338,237. In addition, enhancement of binding specificity for DNA binding domains has been described, for example, in co-owned WO 02/077227.

Selection of target sites; methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., zinc finger binding domains or multi-fingered zinc-finger proteins) may be linked together using any suitable linker sequences, including for example, linkers of 5 or more amino acids in length (e.g., TGEKP (SEQ ID NO:1), TGGQRP (SEQ ID NO:2), TGQKP (SEQ ID NO:3), and/or TGSQKP (SEQ ID NO:4)). See, also, U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein.

As described below, in certain embodiments, the DNA-binding domain (e.g., a four-, five-, or six-finger zinc finger binding domain or a TALE protein comprising 2 or more TALE repeat domains) is fused to a cleavage half-domain, such as, for example, the cleavage domain of a Type IIs restriction endonuclease such as FokI. One or more pairs of such nuclease half-domain fusions are used for targeted cleavage, as disclosed, for example, in U.S. Patent Publication No. 20050064474.

For targeted cleavage using a pair of nucleases, the near edges of the binding sites can separated by 5 or more nucleotide pairs, and each of the fusion proteins can bind to an opposite strand of the DNA target. All pairwise combinations 1 can be used for targeted cleavage of a *Rosa* gene. Following the present disclosure, nucleus can be targeted to any *Rosa* sequence in an animal's genome.

B. Cleavage Domains

The nucleases also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In certain embodiments, two fusion proteins may be required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more DNA-binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using DNA-binding domain-Fok I fusions, two fusion proteins, each comprising a FokI cleavage half-domain, can be used to reconstitute a catalytically active cleavage domain. Alternatively, a single polypeptide molecule containing a DNA-binding domain and two Fok I cleavage half-domains can also be used. Parameters for targeted cleavage and targeted sequence alteration using DNA-binding domain-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., Example 1 of WO 07/139,898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See, U.S. application Ser. No. 12/931,660).

Engineered cleavage half-domains described herein can be prepared using any suitable method, for example, by site-directed mutagenesis of wild-type cleavage half-domains (Fok I) as described in U.S. Patent Publication No. 20050064474.

C. Additional Methods for Targeted Cleavage

Any nuclease having a target site in any *Rosa* gene(s) can be used in the methods disclosed herein. For example, homing endonucleases and meganucleases have very long recognition sequences, some of which are likely to be present, on a statistical basis, once in a human-sized genome. Any such nuclease having a target site in a *Rosa* gene can be used instead of, or in addition to, a TALEN or zinc-finger nuclease, for targeted cleavage.

Exemplary homing endonucleases include I-SceI, I-CeuI, PI-PspI, PI-Sce, I-SceIV, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

Delivery

The nucleases described herein may be delivered to a target cell by any suitable means, including, for example, by injection of nuclease mRNA. See, Hammerschmidt et al. (1999) *Methods Cell Biol.* 59:87-115.

Methods of delivering proteins comprising engineered DNA-binding domains are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases as described herein may also be delivered using vectors containing sequences encoding one or more of the nucleases. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more nuclease encoding sequences. Thus, when one or more pairs of nucleases are introduced into the cell, the nucleases may be carried on the same vector or on different vectors. When multiple vectors are used, each vector may comprise a sequence encoding one or multiple nucleases.

Conventional viral and non-viral based gene transfer methods can be used to introduce nucleic acids encoding engineered DNA-binding domains (e.g., ZFPs or TALEs) in cells. Such methods can also be used to administer nucleic acids encoding DNA-binding domains to cells in vitro. In certain embodiments, nucleic acids encoding the DNA-binding domains are administered for in vivo or ex vivo uses.

Non-viral vector delivery systems include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids. Viral vector delivery systems include DNA and RNA viruses, which have either episomal or integrated genomes after delivery to the cell. Additional exemplary nucleic acid delivery systems include those provided by Amaxa Biosystems (Cologne, Germany), Maxcyte, Inc. (Rockville, Md.), BTX Molecular Delivery Systems (Hollis ton, MA) and Copernicus Therapeutics Inc, (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* vol 27(7) p. 643).

As noted above, the disclosed methods and compositions can be used in any type of cell. Progeny, variants and derivatives of animal cells can also be used.

Applications

The disclosed methods and compositions can be used for genomic editing of any *Rosa* gene or genes. In certain applications, the methods and compositions can be used for inactivation of genomic *Rosa* sequences. In other applications, the methods and compositions allow for generation of random mutations, including generation of novel allelic forms of genes with different expression as compared to unedited genes or integration of humanized genes, which in turn allows for the generation of animal models. In other applications, the methods and compositions can be used for creating random mutations at defined positions of genes that allows for the identification or selection of animals carrying novel allelic forms of those genes.

In other applications, the methods and compositions allow for targeted integration of an exogenous (donor) sequence into any selected area of the genome, for example, a mouse or rat *Rosa* gene. Regulatory sequences (e.g. promoters) could be integrated in a targeted fashion at a site of interest. By "integration" is meant both physical insertion (e.g., into the genome of a host cell) and, in addition, integration by copying of the donor sequence into the host cell genome via the nucleic acid replication processes. Donor sequences can also comprise nucleic acids such as shRNAs, miRNAs etc. These small nucleic acid donors can be used to study their effects on genes of interest within the genome. Additional donor sequences of interest may be human genes which encode proteins relevant to disease models. Non-limiting examples of such genes include human Factor VIII and human Factor IX. Thus insertion of these genes into the *Rosa* locus can allow the researcher to investigate these proteins in greater detail in vivo. Genomic editing (e.g., inactivation, integration and/or targeted or random mutation) of an animal gene can be achieved, for example, by a single cleavage event, by cleavage followed by non-homologous end joining, by cleavage followed by homology-directed repair mechanisms, by cleavage followed by physical integration of a donor sequence, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript. See, U.S. Patent Publication Nos. 20030232410; 20050208489; 20050026157; 20050064474; 20060188987; 20060063231; and International Publication WO 07/014,275, the disclosures of which are incorporated by reference in their entireties for all purposes.

There are a variety of applications for nuclease-mediated genomic editing of a *Rosa* gene. The methods and compositions described herein allow for the generation of models of human diseases. For example, editing of the p53 gene allows for the generation of a "cancer rat" that provides an animal model for studying cancer and testing cancer therapies.

EXAMPLES

Example 1

Construction of Restriction Fragment Length Polymorphism (RFLP) Donor Nucleic Acid for Targeted Integration into the *rRosa* 26 Nucleic Acid Region of the Rat Genome Plasmids were also constructed to target integration of NotI and PmeI RFLP sites into the *rRosa* 26 region of the rat genome. Design and construction of the plasmids was as described in above. The PCR primer pairs used for amplifying the *rRosa* 26 region of homology are described in Table 1.

TABLE 1

Primer sequences

| Name | Sequence |
|---|---|
| rRosa26 200 bp F KpnI | aaaaggtaccgggagtggatgaaggagttg (SEQ ID NO: 5) |
| rRosa26 200 bp R SacII | aaaaccgcggcggatcacaagcaataat (SEQ ID NO: 6) |
| rRose26 target F NotI | cttcgcggccgcgatctgcaactggagtct ttc (SEQ ID NO: 7) |
| rRosa26 target F PmeI | cttcgtttaaacgatctgcaactggagtct ttc (SEQ ID NO: 8) |
| rRosa26 target F NotI | gatcgcggccgcgaagaaggggaagggaa tc (SEQ ID NO: 9) |
| rRosa26 target R PmeI | gatcgtttaaacgaagaaggggaagggaa tc (SEQ ID NO: 10) |
| rRosa26 800 bp F KpnI | aaaaggtaccgcgtgtgaaaacacaaatgg (SEQ ID NO: 11) |
| rRosa26 800 bp R SacII | aaaaccgcggaaggaaagaggcattcatgg (SEQ ID NO: 12) |

TABLE 1-continued

Primer sequences

| Name | Sequence |
|---|---|
| rRosa26 2 Kb F Kpn1 | aaaaggtaccattatggaggggaggactgg (SEQ ID NO: 13) |
| rRosa26 2 Kb R Sac11 | aaaaccgcggacatgtggcaaacaggaga (SEQ ID NO: 14) |
| rRosa26 50 bp F | tgtcttctgaggaccgccc (SEQ ID NO: 15) |
| rRosa26 50 bp R | ctgcccagaagactcccgc (SEQ ID NO: 16) |

Zinc finger designs targeted to the indicated target sites in the rat *Rosa* 26 are shown Tables 2 and 3. Nucleotides in the target site that are contacted by the ZFP recognition helices are indicated in uppercase letters; non-contacted nucleotides indicated in lowercase.

TABLE 2

Rat rosa26 finger designs

| ZFN name | F1 | F2 | F3 | F4 | F5 | F6 |
|---|---|---|---|---|---|---|
| rosa26intron-r885a1 (pair 1) | DRSDLSR (SEQ ID NO: 38) | RSDDLTR (SEQ ID NO: 39) | TSGHLSR (SEQ ID NO: 40) | RSDNLSV (SEQ ID NO: 41) | RSANLTR (SEQ ID NO: 42) | N/A |
| rosa26intron-891a1 (pair 1) | QSDHLTK (SEQ ID NO: 43) | NSSNLSR (SEQ ID NO: 44) | RSDHLTK (SEQ ID NO: 45) | NSDHLSR (SEQ ID NO: 46) | RSDHLSR (SEQ ID NO: 47) | N/A |
| rosa26intron-r887a1 (pair 2) | RSDHLSE (SEQ ID NO: 48) | RSAALAR (SEQ ID NO: 49) | RSDHLST (SEQ ID NO: 50) | QNAHRIT (SEQ ID NO: 51) | RSAVLSE (SEQ ID NO: 52) | N/A |
| rosa26intron-894a1 (pair 2) | QSGDLTR (SEQ ID NO: 17) | TSGSLTR (SEQ ID NO: 18) | RSANLTR (SEQ ID NO: 42) | RSDHLTK (SEQ ID NO: 45) | NSDHLSR (SEQ ID NO: 46) | N/A |
| rosa26intron-r941a1 (pair 3) | RSANLTR (SEQ ID NO: 42) | QSGDLTR (SEQ ID NO: 17) | QSGDLTR (SEQ ID NO: 17) | RSANLAR (SEQ ID NO: 53) | RSDNLRE (SEQ ID NO: 54) | N/A |
| rosa26intron-947a1 (pair 3) | RSDHLST (SEQ ID NO: 50) | DNRDRIK (SEQ ID NO: 55) | RSDTLSE (SEQ ID NO: 56) | QSSHLAR (SEQ ID NO: 57) | QNAHRKT (SEQ ID NO: 22) | N/A |
| rosa26intron-r944a1 (pair 4) | QSGDLTR (SEQ ID NO: 17) | QSGDLTR (SEQ ID NO: 17) | RSDNLTR (SEQ ID NO: 58) | RSDNLSE (SEQ ID NO: 21) | QNAHRKT (SEQ ID NO: 22) | N/A |
| rosa26intron-950a1 (pair 4) | DRSDLSR (SEQ ID NO: 38) | RSDHLST (SEQ ID NO: 50) | DNRDRIK (SEQ ID NO: 55) | RSDTLSE (SEQ ID NO: 56) | QSSHLAR (SEQ ID NO: 57) | N/A |
| rosa26intron-r951a1 (pair 5) | QSGDLTR (SEQ ID NO: 17) | RSDNLTR (SEQ ID NO: 58) | RSDNLSE (SEQ ID NO: 21) | QNAHRKT (SEQ ID NO: 22) | RSDHLSE (SEQ ID NO: 48) | TSSTRKT (SEQ ID NO: 59) |
| rosa26intron-958a1 (pair 5) | TSGNLTR (SEQ ID NO: 60) | QSGNLAR (SEQ ID NO: 61) | RSDALSV (SEQ ID NO: 62) | DSSHRTR (SEQ ID NO: 63) | RSDVLSE (SEQ ID NO: 64) | N/A |
| rosa26intron-r954a1 (pair 6) | RSDNLSE (SEQ ID NO: 21) | QNAHRKT (SEQ ID NO: 22) | RSDHLSE (SEQ ID NO: 48) | TSSTRKT (SEQ ID NO: 59) | TSGHLSR (SEQ ID NO: 40) | N/A |
| rosa26intron-961a1 (pair 6) | TSGNLTR (SEQ ID NO: 60) | QSGNLAR (SEQ ID NO: 61) | RSDALSV (SEQ ID NO: 62) | DSSHRTR (SEQ ID NO: 63) | N/A | N/A |
| rosa26intron-r983a1 (pair 7) | QRSNLVR (SEQ ID NO: 65) | RSDHLTQ (SEQ ID NO: 66) | QSGHLQR (SEQ ID NO: 67) | DRSHLAR (SEQ ID NO: 68) | N/A | N/A |
| rosa26intron-989a1 (pair 7) | RSDVLSE (SEQ ID NO: 64) | QRNHRTT (SEQ ID NO: 69) | TKRSLIE (SEQ ID NO: 70) | TSSNLSR (SEQ ID NO: 71) | RSDDLSK (SEQ ID NO: 25) | DNRDRIK (SEQ ID NO: 55) |

TABLE 2-continued

Rat rosa26 finger designs

| ZFN name | F1 | F2 | F3 | F4 | F5 | F6 |
|---|---|---|---|---|---|---|
| rosa26intron-r989a1 (pair 8) | RSDHLSA (SEQ ID NO: 72) | QSGHLSR (SEQ ID NO: 24) | RSDHLSR (SEQ ID NO: 47) | QNDNRIK (SEQ ID NO: 73) | QSGNLAR (SEQ ID NO: 61) | N/A |
| rosa26intron-996a1 (pair 8) | NNRDLIN (SEQ ID NO: 74) | TSSNLSR (SEQ ID NO: 71) | RSDVLSE (SEQ ID NO: 64) | QRNHRTT (SEQ ID NO: 69) | TKRSLIE (SEQ ID NO: 70) | TSSNLSR (SEQ ID NO: 71) |

TABLE 3 rat rosa26 target sites

| ZFN name | Target sequence |
|---|---|
| rosa26intron-r885a1 (pair 1) | ctGAGAAGGGTGCGGCCttttctccgcc (SEQ ID NO: 75) |
| rosa26intron-891a1 (pair 1) | acGGGGGAGGGGAGTGTtgcaataccttt (SEQ ID NO: 76) |
| rosa26intron-r887a1 (pair 2) | tcCTGAGAAGGGTGCGGccttttctccg (SEQ ID NO: 77) |
| rosa26intron-894a1 (pair 2) | ggGGAGGGGAGtGTTGCAataccttttct (SEQ ID NO: 78) |
| rosa26intron-r941a1 (pair 3) | gaCAGGAGGCAGCAGAGaactcccagaa (SEQ ID NO: 79) |
| rosa26intron-947a1 (pair 3) | tcTGAGGACCGCCCTGGgcctggaagat (SEQ ID NO: 80) |
| rosa26intron-r944a1 (pair 4) | gaAGACAGGAGGCAGCAgagaactccca (SEQ ID NO: 81) |
| rosa26intron-950a1 (pair 4) | gaGGACCGCCCTGGGCCtggaagattcc (SEQ ID NO: 82) |
| rosa26intron-r951a1 (pair 5) | gtCCTCAGaAGACAGGAGGCAgcagaga (SEQ ID NO: 83) |
| rosa26intron-958a1 (pair 5) | ccCTGGGCCTGGAAGATtcccttccccc (SEQ ID NO: 84) |
| rosa26intron-r954a1 (pair 6) | gcGGTCCTCAGaAGACAGgaggcagcag (SEQ ID NO: 85) |
| rosa26intron-961a1 (pair 6) | tgGGCCTGGAAGATtcccttccccttc (SEQ ID NO: 86) |
| rosa26intron-r983a1 (pair 7) | aaGGGGGAAGGGAAtcttccaggcccag (SEQ ID NO: 87) |
| rosa26intron-989a1 (pair 7) | ttCCCTCGtGATCTGCAACTGgagtctt (SEQ ID NO: 88) |
| rosa26intron-r989a1 (pair 8) | ggGAAGAAGGGGAAGGgaatcttccag (SEQ ID NO: 89) |
| rosa26intron-996a1 (pair 8) | gtGATCTGCAACTGGAGTCTttctggaa (SEQ ID NO: 90) |

Rat C6 cells were transfected with GFP control or each of the 8 pairs of ZFNs. DNA was prepared from the cells one day post transfection. ZFN cleavage was assayed with the Surveyor™ nuclease as described, for example, in U.S. Patent Publication Nos. 20080015164; 20080131962 and 20080159996, using the products amplified with respective primers (SEQ ID NOS 91-92). The results are presented in FIG. 1. Arrows indicate cleavage was found only in samples containing ZFN pairs, but was not found in the control samples wherein cells were transfected with ZFNs specific for GFP.

Example 2

Zinc Finger Nucleases Specific for the Mouse *Rosa* 26 Locus

Zinc finger designs targeted to the indicated target sites in the mouse *Rosa* 26 are shown Tables 4 and 5. Nucleotides in the target site that are contacted by the ZFP recognition helices are indicated in uppercase letters; non-contacted nucleotides indicated in lowercase.

TABLE 4 mouse Rosa26 zinc finger designs

| ZFN name | F1 | F2 | F3 | F4 | F5 | F6 |
|---|---|---|---|---|---|---|
| 18477 | QSGDLTR (SEQ ID NO: 17) | TSGSLTR (SEQ ID NO: 18) | QSGHLAR (SEQ ID NO: 19) | QSSDLTR (SEQ ID NO: 20) | RSDNLSE (SEQ ID NO: 21) | QNAHRKT (SEQ ID NO: 22) |
| 18473 | DRSARTR (SEQ ID NO: 23) | QSGHLSR (SEQ ID NO: 24) | RSDDLSK (SEQ ID NO: 25) | RNDHRKN (SEQ ID NO: 26) | N/A | N/A |
| 25096 | DTTSLDR (SEQ ID NO: 27) | TSGSLTR (SEQ ID NO: 18) | QSGHLAR (SEQ ID NO: 19) | QSSDLTR (SEQ ID NO: 20) | RSDNLSE (SEQ ID NO: 21) | QNAHRKT (SEQ ID NO: 22) |

TABLE 5 mouse Rosa26 target sites

| ZFN name | Target sequence |
|---|---|
| 18477 | ctAGAAAGACTGGAGTTGCAgatcacga (SEQ ID NO: 28) |
| 18473 | gaTGGGCGGGAGTCttctgggcaggctt (SEQ ID NO: 29) |
| 25096 | ctAGAAAGACTGGAGTTGCAgatcacga (SEQ ID NO: 30) |

Cel-I analysis was conducted as described above for ZFN pairs 18473/18477 and 18473/25096 and the percent NHEJ seen was as follows: 26.5% NHEJ using ZFN pair 18477/18473 and 35.70% NHEJ with ZFN pair 18473/25096.

Example 3

Targeted Integration of a Donor Polynucleotide into Rosa 26 Locus of the Mouse Genome Rosa donors were constructed by cloning of PCR products made using the following oligonucleotides: for 527 bp left arms, the oligonucleotides used for PCR were 5'-ggc tcg agt gag tca tca gac ttc taa gat cag g-3' (SEQ ID NO:31); for 413 bp left-arm donors, 5'-ggc tcg agt ttt gat aag gct gca gaa g-3' (SEQ ID NO:32) in conjunction with the reverse primer 5'-ctg aat tcg aat ggg cgg gag tct tct ggg ca-3' (SEQ ID NO:33).

For 640 bp right arms, the oligonucleotides used for PCR were 5'-cca agc ttg gag gta ggt ggg gtg agg-3' (SEQ ID NO:34); for 200 bp arms, 5'-cca agc tta gtc gct ctg agt tgt tat c-3' (SEQ ID NO:35); for 100 bp arms, 5'-cca agc ttt ctg gga gtt ctc tgc tgc c-3' (SEQ ID NO:36) in conjunction with the reverse primer 5'-cat tcg aat tca gaa aga ctg gag ttg cag atc-3' (SEQ ID NO:37). Individual arm'amplicons were joined via fusion PCR and cloned to produce donors with varying homology arms. Neuro2a cells (200,000) were co-transfected with 400 ng each of SBS 18473 and 18477 along with 2 µg of the indicated donor in solution SF using the Amaxa-Shuttle Neuro2a high efficiency protocol.

Genomic DNA was harvested 72 hours after transfection and 100 ng used for PCR with 5'-cccagctacagcctcgattt-3' (SEQ ID NO: 91), 5'-cacaaatggcgtgttttggt-3' (SEQ ID NO: 92) and 5 µCi of both 32P-dATP and 32P-dCTP per sample at an annealing temperature of 68° C. with a two minute extension at 72° C. for 28 cycles. Following G-50 column purification, 10 µL of each 50 µL reaction was digested with EcoRI at 37° C. for two hours and loaded onto a 10% polyacrylamide gel.

Figure 2:
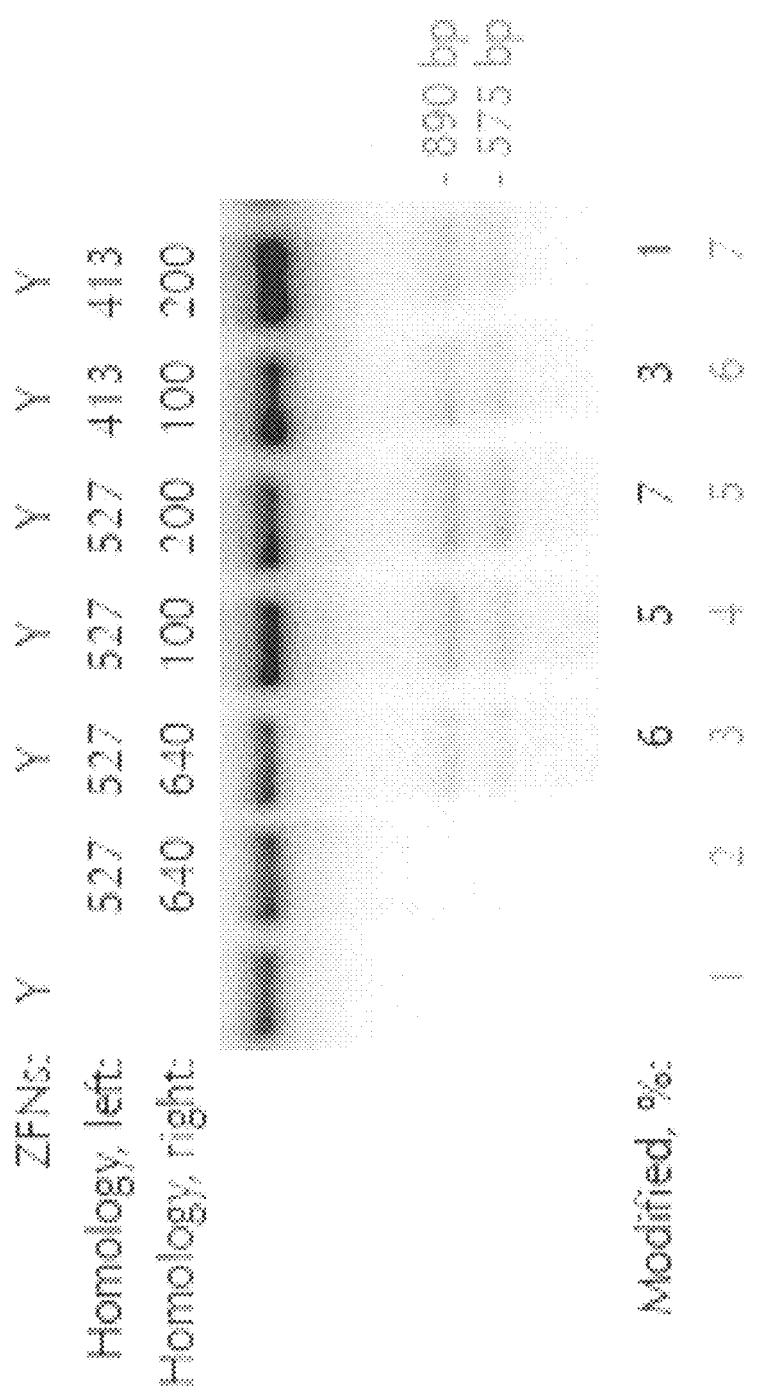
FIG. 2 depicts insertion of *Rosa* -targeted donor nucleotides into mouse genomic DNA.

As shown in FIG. 2, the donor nucleotides were inserted into the Rosa locus at the indicated frequencies.

Example 4

Rosa Modification Using TALENs

Rosa-targeted TALENs with N-cap and C-cap polypeptides and with at least 12 TALE repeats (that bind to 12 contiguous nucleotides) are constructed to rodent Rosa target sites, essentially as described in U.S. Publication No. 20110301073, incorporated by reference herein in its entirety. These TALENs are used to modify the targeted Rosa gene in a host cell (e.g., embryo), for example by insertion of a donor sequence and/or via non-homologous end joining of the cleavage site(s).

The TALEN modified cells are used in vitro assays, for example, drug discovery. Similarly, TALEN-modified embryos are used to generate animal models.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated fusion protein comprising a FokI nuclease domain and one or more TAL effector (TALE) polypeptides comprising a plurality of TALE repeat domains, wherein each TALE repeat domain comprises a RVD, wherein:
   (i) each RVD of said TALE repeat domains bind to a target site in a *Rosa* gene, wherein said target site is selected from the group consisting of the nucleotide sequence of SEQ ID NO: 28, SEQ ID NO: 29, SEQ ID NO: 79, SEQ ID NO: 80, SEQ ID NO: 81, SEQ ID NO: 82, SEQ ID NO: 87, SEQ ID NO: 88, SEQ ID NO: 89, and SEQ ID NO: 90: and further wherein said RVD comprises the amino acids NI, HI, AI, CI, DI, EI, RI or KI which recognizes adenine (A) in said target site; the amino acids HD, AD, KD, YD, ED, AD, ND or RD which recognizes cytosine (C) in said target site; the amino acids NN, DK, DH, KN, EN, AN, CN, GN, FN, AK, NK or CK which recognizes guanine (G) in said target site; and the amino acids NG, KG MG, QG, RG, AA, QA, IG, IP, LA, YG, HG, SG, VG, IA or VA which recognizes thymine (T) in said target site; and
   (ii) said fusion protein cleaves said *Rosa* gene.

2. The isolated fusion protein of claim 1, wherein said FokI nuclease domain is naturally occurring or engineered.

3. A polynucleotide encoding said isolated fusion protein of claim 1.

4. An isolated cell comprising said isolated fusion protein of claim 1, wherein said isolated cell is not a human embryonic cell.

5. An isolated cell comprising the polynucleotide of claim 3, wherein said isolated cell is not a human embryonic cell.

6. The isolated cell of claim 4, wherein said isolated cell is a rat or mouse embryonic cell.

7. A composition comprising said isolated fusion protein of claim 1 and a pharmaceutically acceptable excipient.

8. A composition comprising said polynucleotide of claim 3 and a pharmaceutically acceptable excipient.

9. A method for cleaving one or more *Rosa* genes in an isolated rat or mouse cell, said method comprising:
   introducing into said isolated rat or mouse cell, one or more isolated fusion proteins of claim 1 into said isolated rat or mouse cell, such that the one or more *Rosa* gene are cleaved.

10. The method of claim 9, wherein said one or more fusion proteins are introduced by transforming said isolated rat or mouse cell with polynucleotides encoding said isolated fusion proteins.

11. A method of introducing an exogenous polynucleotide sequence into the genome of an isolated rat or mouse cell, said method comprising:
   cleaving one or more *Rosa* genes by the method of claim 9; and
   contacting said isolated rat or mouse cell with an exogenous polynucleotide sequence;
   wherein cleavage of said one or more *Rosa* genes stimulates integration of said exogenous polynucleotide sequence into the genome of said isolated cell by homologous recombination.

12. The method of claim 11, wherein said exogenous polynucleotide sequence is integrated into the genome via nucleic acid replication processes.

13. The method of claim 11, wherein said exogenous polynucleotide sequence is integrated into the genome via non-homology dependent targeted integration.

14. A method of modifying a *Rosa* gene sequence in the genome of an isolated rat or mouse cell, said method comprising:
   cleaving one or more *Rosa* genes by the method of claim 9, wherein said cleavage results in a modification of said *Rosa* gene sequence by non-homologous end joining or homology directed repair.

15. The method of claim 14, wherein said modification comprises a deletion.

16. The method of claim 14, wherein said modification comprises insertion of an exogenous sequence.

17. A kit comprising the isolated fusion protein of claim 1.

18. A kit comprising the polynucleotide of claim 3.

19. The kit of claim 17, further comprising additional components selected from the group consisting of one or more exogenous sequences, instructions for use, and combinations thereof.

20. The kit of claim 18, further comprising additional components selected from the group consisting of one or more exogenous sequences, instructions for use, and combinations thereof.

* * * * *